(12) United States Patent
Barker

(10) Patent No.: US 9,425,537 B2
(45) Date of Patent: *Aug. 23, 2016

(54) SYSTEMS AND METHODS FOR MAKING AND USING A SIDE-LOADING OPERATING ROOM CABLE OF AN ELECTRICAL STIMULATION SYSTEM

(71) Applicant: Boston Scientific Neuromodulation Corporation, Valencia, CA (US)

(72) Inventor: John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/752,523

(22) Filed: Jun. 26, 2015

(65) Prior Publication Data
US 2015/0303609 A1 Oct. 22, 2015

Related U.S. Application Data

(63) Continuation of application No. 13/655,874, filed on Oct. 19, 2012, now Pat. No. 9,101,755.

(60) Provisional application No. 61/549,010, filed on Oct. 19, 2011.

(51) Int. Cl.
*A61N 1/00* (2006.01)
*H01R 13/502* (2006.01)
*A61N 1/375* (2006.01)
(Continued)

(52) U.S. Cl.
CPC ............. *H01R 13/502* (2013.01); *A61N 1/05* (2013.01); *A61N 1/3752* (2013.01); *A61N 1/048* (2013.01); *A61N 1/0476* (2013.01); *A61N 1/0488* (2013.01);
(Continued)

(58) Field of Classification Search
USPC ...................................... 607/36, 115
See application file for complete search history.

(56) References Cited

U.S. PATENT DOCUMENTS 5,354,326 A  10/1994 Comben et al.
5,782,892 A   7/1998 Castle et al.
(Continued)

FOREIGN PATENT DOCUMENTS

WO    2012/075497    6/2012

OTHER PUBLICATIONS

Official Communication for U.S. Appl. No. 13/655,874 mailed Jan. 23, 2015.
(Continued)

*Primary Examiner* — Nicole F Lavert
(74) *Attorney, Agent, or Firm* — Lowe Graham Jones PLLC; Bruce E. Black

(57) ABSTRACT

An operating room cable for electrically coupling a lead to a trial stimulator includes a trial stimulator connector electrically coupleable with the trial stimulator and a lead connector for receiving the lead. The lead connector includes a housing. A first lead aperture is defined in a second end of the housing in proximity to a first side of the housing. A first inner passage extends along an interior of the housing from the first lead aperture to the second end of the housing. A first stylet slit is defined along the first side of the housing and extends from a first end of the housing to the second end of the housing. The first stylet slit is formed between upper and lower casings of the housing. The first stylet slit is continuous with the first lead aperture and the first inner passage.

20 Claims, 14 Drawing Sheets

(51) Int. Cl.
*A61N 1/05* (2006.01)
*A61N 1/04* (2006.01)
*A61N 1/36* (2006.01)

(52) U.S. Cl.
CPC .......... *A61N 1/3605* (2013.01); *Y10T 29/49117* (2015.01)

(56) References Cited

U.S. PATENT DOCUMENTS

| | | | |
|---|---|---|---|
| 5,931,861 | A | 8/1999 | Werner et al. |
| 6,038,479 | A | 3/2000 | Werner et al. |
| 6,038,481 | A | 3/2000 | Werner et al. |
| 6,181,969 | B1 | 1/2001 | Gord |
| 6,192,278 | B1 | 2/2001 | Werner et al. |
| 6,343,233 | B1 | 1/2002 | Werner et al. |
| 6,397,108 | B1 | 5/2002 | Camps et al. |
| 6,516,227 | B1 | 2/2003 | Meadows et al. |
| 6,609,029 | B1 | 8/2003 | Mann et al. |
| 6,609,032 | B1 | 8/2003 | Woods et al. |
| 6,687,538 | B1 | 2/2004 | Hrdlicka et al. |
| 6,741,892 | B1 | 5/2004 | Meadows et al. |
| 6,950,709 | B2 | 9/2005 | Baudino |
| 6,980,863 | B2 | 12/2005 | van Venrooij et al. |
| 7,244,150 | B1 | 7/2007 | Brase et al. |
| 7,437,193 | B2 | 10/2008 | Parramon et al. |
| 7,493,159 | B2 | 2/2009 | Hrdlicka et al. |
| 7,539,542 | B1 | 5/2009 | Malinowski |
| 7,548,788 | B2 | 6/2009 | Chinn et al. |
| 7,563,141 | B2 | 7/2009 | Alexander et al. |
| 7,594,828 | B2 | 9/2009 | Alexander et al. |
| 7,633,023 | B1 | 12/2009 | Cappa et al. |
| 7,672,734 | B2 | 3/2010 | Anderson et al. |
| 7,736,192 | B2 | 6/2010 | Alexander et al. |
| 7,761,165 | B1 | 7/2010 | He et al. |
| 7,949,395 | B2 | 5/2011 | Kuzma |
| 7,974,706 | B2 | 7/2011 | Moffitt et al. |
| 8,175,710 | B2 | 5/2012 | He |
| 8,224,450 | B2 | 7/2012 | Brase |
| 8,239,042 | B2 | 8/2012 | Chinnn et al. |
| 8,364,278 | B2 | 1/2013 | Pianca et al. |
| 8,401,670 | B2 | 3/2013 | Mehdizadeh et al. |
| 8,849,396 | B2 | 9/2014 | DeRohan et al. |
| 9,101,775 | B2 | 8/2015 | Barker |
| 2003/0199948 | A1 | 10/2003 | Kokones et al. |
| 2004/0106964 | A1* | 6/2004 | Fischer, Sr. .............. A61N 1/05 607/36 |
| 2005/0165465 | A1 | 7/2005 | Pianca et al. |
| 2007/0150036 | A1 | 6/2007 | Anderson |
| 2007/0197896 | A1* | 8/2007 | Moll ................... A61B 1/00039 600/407 |
| 2010/0070012 | A1 | 3/2010 | Chinn et al. |
| 2010/0106204 | A1 | 4/2010 | Moffitt et al. |
| 2010/0249869 | A1* | 9/2010 | Ries ................... A61N 1/3752 607/37 |
| 2011/0098795 | A1 | 4/2011 | Mehdizadeh et al. |
| 2011/0218549 | A1 | 9/2011 | Barker |
| 2013/0098678 | A1 | 4/2013 | Barker |
| 2015/0025609 | A1 | 1/2015 | Govea |

OTHER PUBLICATIONS

U.S. Appl. No. 14/962,938, filed Dec. 8, 2015.
U.S. Appl. No. 14/992,931, filed Jan. 11, 2016.

* cited by examiner

SYSTEMS AND METHODS FOR MAKING AND USING A SIDE-LOADING OPERATING ROOM CABLE OF AN ELECTRICAL STIMULATION SYSTEM

CROSS-REFERENCE TO RELATED APPLICATIONS

This application is a continuation of U.S. patent application Ser. No. 13/655,874 filed Oct. 19, 2012 which claims the benefit under 35 U.S.C. §119(e) of U.S. Provisional Patent Application Ser. No. 61/549,010 filed on Oct. 19, 2011, both of which are incorporated herein by reference.

FIELD

The present invention is directed to the area of implantable electrical stimulation systems and methods of making and using the systems. The present invention is also directed to an improved operating room cable configured and arranged to electrically couple an implanted lead to a trial stimulator, as well as methods of making and using the system, operating room cable, and lead.

BACKGROUND

Implantable electrical stimulation systems have proven therapeutic in a variety of diseases and disorders. For example, deep brain stimulation and spinal cord stimulation systems have been used as therapeutic modalities for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, an operating room cable for electrically coupling at least one electrical stimulation lead to a trial stimulator includes an elongated body having a first end and an opposing second end. A trial stimulator connector is disposed at the first end of the body and is electrically coupleable with the trial stimulator. A lead connector is disposed at the second end of the body and is electrically coupled to the trial stimulator connector. The lead connector is configured and arranged to mechanically receive a proximal end of at least one electrical stimulation lead. The lead connector includes a housing having an upper casing and a lower casing coupled to the upper casing. The upper casing has an upper major surface and the lower casing has a lower major surface that opposes the upper major surface. The upper and lower casings collectively form a perimeter section extending between the upper major surface and the lower major surface. The perimeter section includes an elongated first side, an elongated second side opposing the first side, a first end extending between the first side and the second side, and a second end opposing the first end. A first lead aperture is defined in the second end of the housing in proximity to the first side of the housing. A first inner passage extends along an interior of the housing from the first lead aperture to the second end of the housing. A first stylet slit is defined along the first side of the housing and extends from the first end of the housing to the opposing second end of the housing. The first stylet slit is formed along an interface between the upper casing and the lower casing with the upper casing forming a first wall of the first stylet slit and the lower casing forming an opposing second wall of the first stylet slit. The first stylet slit is continuous with the first lead aperture and the first inner passage.

In another embodiment, a trial stimulation arrangement for an electrical stimulation system includes an operating room cable and a trial stimulator. The operating room cable is for electrically coupling at least one electrical stimulation lead to a trial stimulator, and includes an elongated body having a first end and an opposing second end. A trial stimulator connector is disposed at the first end of the body and is electrically coupleable with the trial stimulator. A lead connector is disposed at the second end of the body and is electrically coupled to the trial stimulator connector. The lead connector is configured and arranged to mechanically receive a proximal end of at least one electrical stimulation lead. The lead connector includes a housing having an upper casing and a lower casing coupled to the upper casing. The upper casing has an upper major surface and the lower casing has a lower major surface that opposes the upper major surface. The upper and lower casings collectively form a perimeter section extending between the upper major surface and the lower major surface. The perimeter section includes an elongated first side, an elongated second side opposing the first side, a first end extending between the first side and the second side, and a second end opposing the first end. A first lead aperture is defined in the second end of the housing in proximity to the first side of the housing. A first inner passage extends along an interior of the housing from the first lead aperture to the second end of the housing. A first stylet slit is defined along the first side of the housing and extends from the first end of the housing to the opposing second end of the housing. The first stylet slit is formed along an interface between the upper casing and the lower casing with the upper casing forming a first wall of the first stylet slit and the lower casing forming an opposing second wall of the first stylet slit. The first stylet slit is continuous with the first lead aperture and the first inner passage. The trial stimulator is configured and arranged to generate electrical stimulation signals. The trial stimulator is disposed external to a patient and is coupleable to the trial stimulation connector of the operating room cable. A first electrical stimulation lead has a distal end, a proximal end, a longitudinal length, and a diameter. The first lead includes a plurality of electrodes disposed on the distal end of the first lead; a plurality of terminals disposed on the proximal end of the first lead; and a plurality of conductors, each conductor electrically coupling at least one of the electrodes to at least one of the terminals. The proximal end of the first lead is insertable into the first lead aperture of the operating room cable.

In yet another embodiment, a method for performing a trial stimulation on a patient includes providing an operating room cable. The operating room cable includes an elongated body having a first end and an opposing second end. A trial stimulator connector is disposed at the first end of the body and is electrically coupleable with the trial stimulator. A lead connector is disposed at the second end of the body and is electrically coupled to the trial stimulator connector. The lead connector is configured and arranged to mechanically receive a proximal end of at least one electrical stimulation lead. The lead connector includes a housing having an upper casing and a lower casing coupled to the upper casing. The upper casing has an upper major surface and the lower casing has a lower major surface that opposes the upper major surface. The upper and lower casings collectively form a perimeter section extending between the upper major surface and the lower major surface. The perimeter section includes an elongated first side, an elongated second side opposing the first side, a first end extending between the first side and the second side, and a second end opposing the first end. A first lead aperture is defined in the second end of the housing in proximity to the first side of the housing. A first inner passage extends along an interior of the housing from the first lead aperture to the second end of the housing. A first stylet slit is defined along the first side of the housing and extends from the first end of the housing to the opposing second end of the housing. The first stylet slit is formed along an interface between the upper casing and the lower casing with the upper casing forming a first wall of the first stylet slit and the lower casing forming an opposing second wall of the first stylet slit. The first stylet slit is continuous with the first lead aperture and the first inner passage. A proximal end of a first stylet is partially retracted from a proximal end of a first electrical stimulation lead. The exposed portion of the partially retracted first stylet is inserted into the first stylet slit of the operating room cable such that the proximal end of the first lead is disposed in proximity to the second end of the lead connector and a first handle disposed on the proximal end of the first stylet extends from the first end of the lead connector. The proximal end of the first lead is inserted into the first lead aperture of the lead connector until the proximal end of the first lead contacts a first end stop disposed in the first inner passage of the lead connector. A first locking feature of the operating room cable is moved along a first locking slit to lock a plurality of first pin connectors to terminals disposed on the received portion of the first lead. The trial stimulator connector of the operating room cable is electrically coupled to a trial stimulator.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to an improved operating room cable configured and arranged to electrically couple an implanted lead to a trial stimulator, as well as methods of making and using the system, operating room cable, and lead.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; 7,974,706; 8,175,710; and 8,224,450; and U.S. Patent Application Publication Nos. 2005/0165465; and 2007/0150036, all of which are incorporated by reference.

Figure 1:
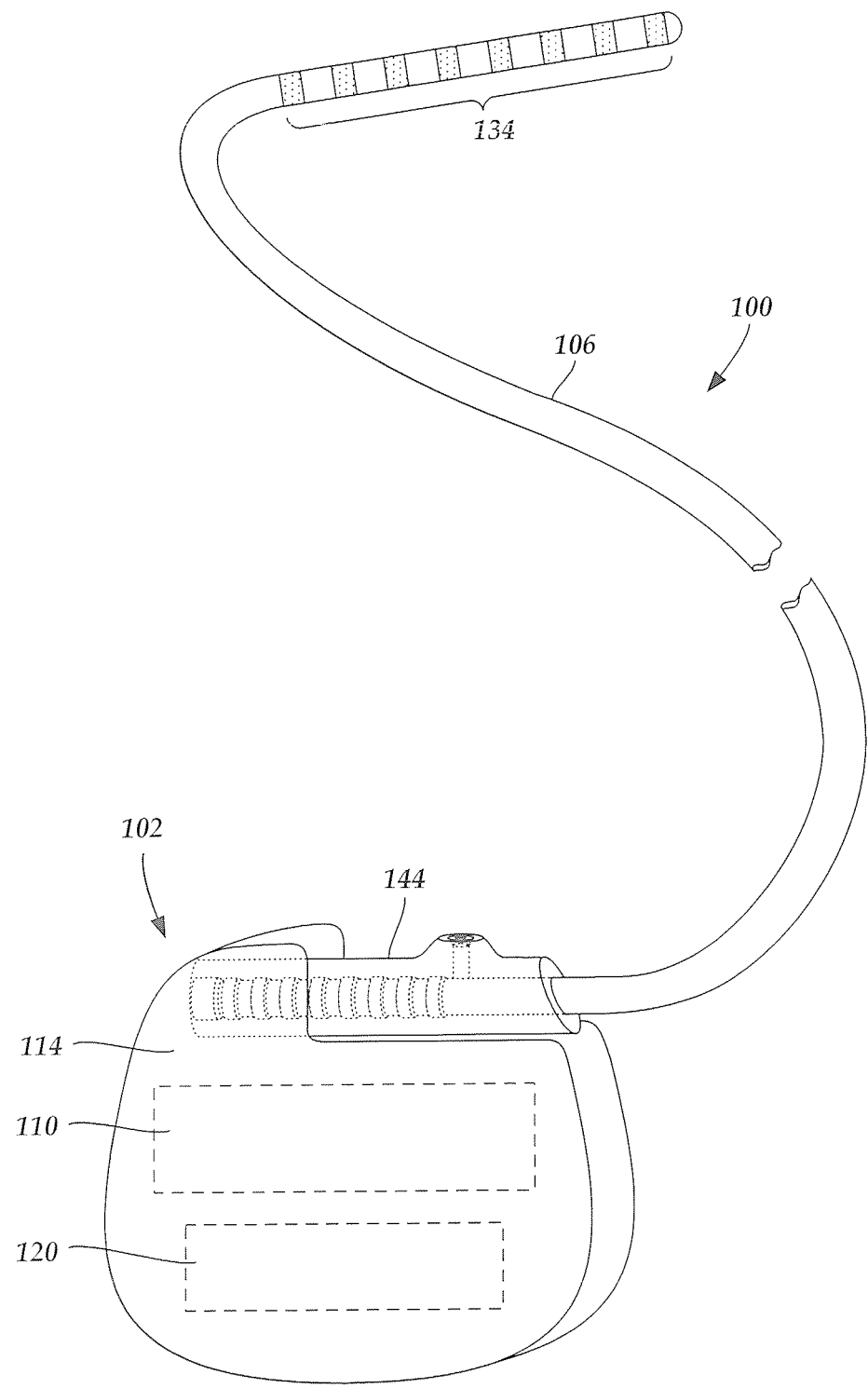
FIG. 1 is a schematic view of one embodiment of an electrical stimulation system, according to the invention.

FIG. 1 illustrates schematically one embodiment of an electrical stimulation system 100. The electrical stimulation system includes a control module (e.g., a stimulator or pulse generator) 102 and at least one lead 106 coupled to the control module 102. Each lead 106 typically includes an array of electrodes 134. The control module 102 typically includes an electronic subassembly 110 and an optional power source 120 disposed in a sealed housing 114. The control module 102 typically includes a connector 144 (FIG. 2A, see also 222 and 250 of FIG. 2B) into which the proximal end of the one or more leads 106 can be plugged to make an electrical connection via conductive contacts on the control module 102 and terminals (e.g., 210 in FIG. 2A and 236 of FIG. 2B) on each of the one or more leads 106. In at least some embodiments, a lead is isodiametric along a longitudinal length of the lead 106. In addition, one or more lead extensions 224 (see FIG. 2B) can be disposed between the one or more leads 106 and the control module 102 to extend the distance between the one or more leads 106 and the control module 102 of the embodiment shown in FIG. 1.

The electrical stimulation system or components of the electrical stimulation system, including one or more of the leads 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of one or more leads 106 are typically disposed in, or separated by, a non-conductive, biocompatible material such as, for example, silicone, polyurethane, polyetheretherketone ("PEEK"), epoxy, and the like or combinations thereof. The leads 106 may be formed in the desired shape by any process including, for example, molding (including injection molding), casting, and the like. The non-conductive material typically extends from the distal end of the one or more leads 106 to the proximal end of each of the one or more leads 106.

Terminals (e.g., 210 in FIG. 2A and 236 of FIG. 2B) are typically disposed at the proximal end of the one or more leads 106 of the electrical stimulation system 100 for connection to corresponding conductive contacts (e.g., 214 in FIG. 2A and 240 of FIG. 2B) in connectors (e.g., 144 in FIGS. 1-2A and 222 and 250 of FIG. 2B) disposed on, for example, the control module 102 (or to conductive contacts on a lead extension, an operating room cable, or an adaptor). Conductor wires (not shown) extend from the terminals (e.g., 210 in FIG. 2A and 236 of FIG. 2B) to the electrodes 134. Typically, one or more electrodes 134 are electrically coupled to a terminal (e.g., 210 in FIG. 2A and 236 of FIG. 2B). In at least some embodiments, each terminal (e.g., 210 in FIG. 2A and 236 of FIG. 2B) is only connected to one electrode 134.

The conductor wires may be embedded in the non-conductive material of the lead 106 or can be disposed in one or more lumens (not shown) extending along the lead 106. In some embodiments, there is an individual lumen for each conductor wire. In other embodiments, two or more conductor wires may extend through a lumen. There may also be one or more lumens (not shown) that open at, or near, the proximal end of the lead 106, for example, for inserting a stylet wire to facilitate placement of the lead 106 within a body of a patient. Additionally, there may also be one or more lumens (not shown) that open at, or near, the distal end of the lead 106, for example, for infusion of drugs or medication into the site of implantation of the one or more leads 106. In at least one embodiment, the one or more lumens may be flushed continually, or on a regular basis, with saline, epidural fluid, or the like. In at least some embodiments, the one or more lumens can be permanently or removably sealable at the distal end.

Figure 2A:
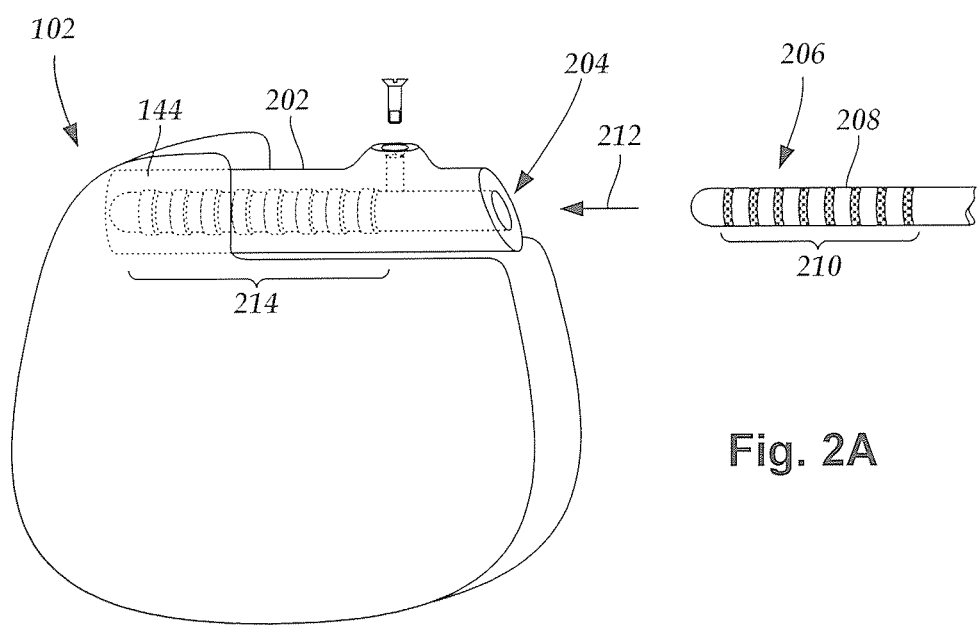
FIG. 2A is a schematic view of one embodiment of a proximal portion of a lead and a control module of an electrical stimulation system, according to the invention.

In at least some embodiments, leads are coupled to connectors disposed on control modules. In FIG. 2A, a lead 208 is shown configured and arranged for insertion to the control module 102. The connector 144 includes a connector housing 202. The connector housing 202 defines at least one port 204 into which a proximal end 206 of a lead 208 with terminals 210 can be inserted, as shown by directional arrow 212. The connector housing 202 also includes a plurality of conductive contacts 214 for each port 204. When the lead 208 is inserted into the port 204, the conductive contacts 214 can be aligned with the terminals 210 on the lead 208 to electrically couple the control module 102 to the electrodes (134 of FIG. 1) disposed at a distal end of the lead 208. Examples of connectors in control modules are found in, for example, U.S. Pat. Nos. 7,244,150 and 8,224,450, which are incorporated by reference.

Figure 2B:
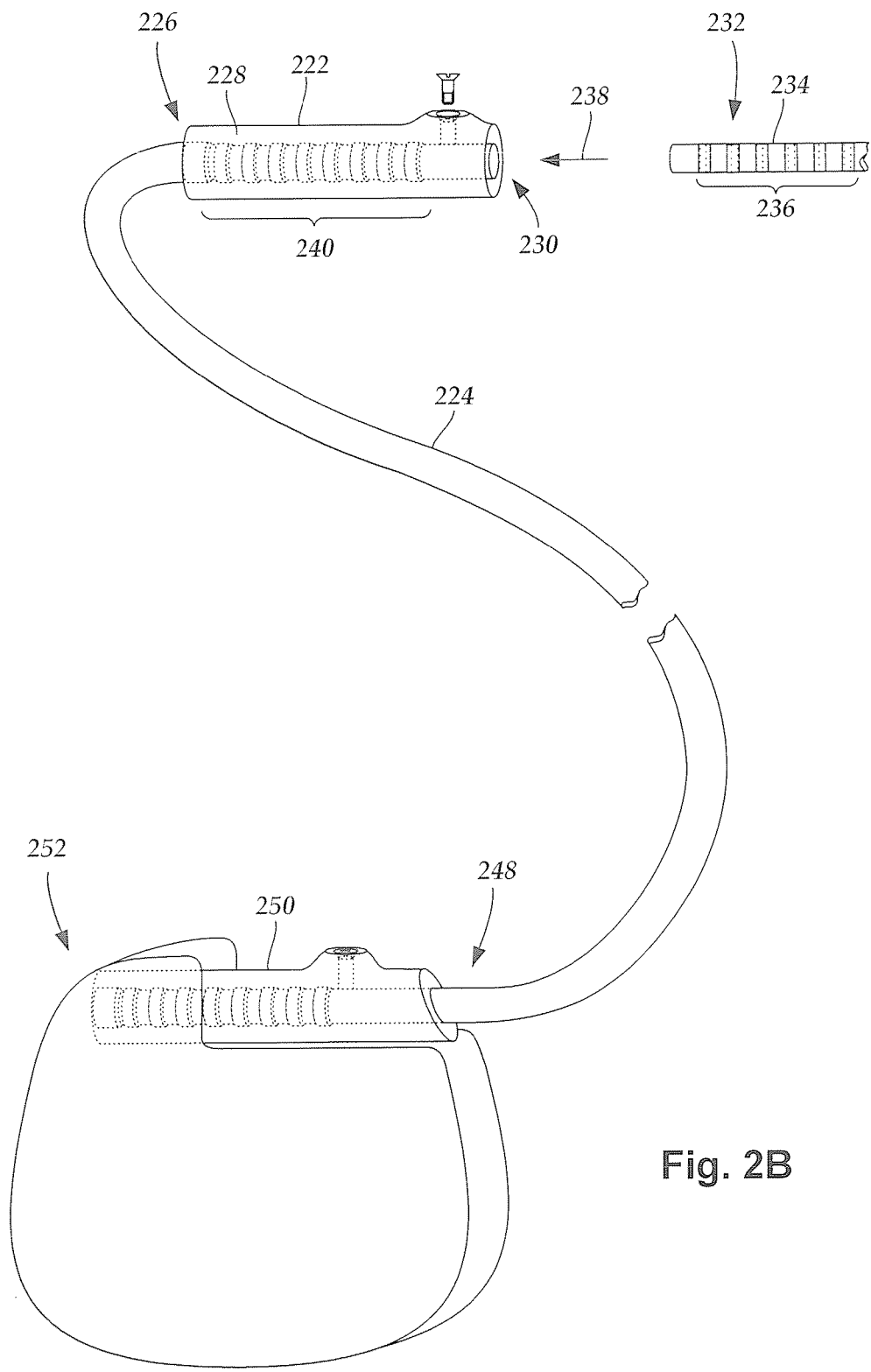
FIG. 2B is a schematic view of one embodiment of a proximal portion of a lead and a lead extension of an electrical stimulation system, according to the invention.

In FIG. 2B, a connector 222 is disposed on a lead extension 224. The connector 222 is shown disposed at a distal end 226 of the lead extension 224. The connector 222 includes a connector housing 228. The connector housing 228 defines at least one port 230 into which a proximal end 232 of a lead 234 with terminals 236 can be inserted, as shown by directional arrow 238. The connector housing 228 also includes a plurality of conductive contacts 240. When the lead 234 is inserted into the port 230, the conductive contacts 240 disposed in the connector housing 228 can be aligned with the terminals 236 on the lead 234 to electrically couple the lead extension 224 to the electrodes (134 of FIG. 1) disposed at a distal end (not shown) of the lead 234.

In at least some embodiments, the proximal end of a lead extension is similarly configured and arranged as a proximal end of a lead. The lead extension 224 may include a plurality of conductive wires (not shown) that electrically couple the conductive contacts 240 to a proximal end 248 of the lead extension 224 that is opposite to the distal end 226. In at least some embodiments, the conductive wires disposed in the lead extension 224 can be electrically coupled to a plurality of terminals (not shown) disposed on the proximal end 248 of the lead extension 224. In at least some embodiments, the proximal end 248 of the lead extension 224 is configured and arranged for insertion into a connector disposed in another lead extension. In other embodiments, the proximal end 248 of the lead extension 224 is configured and arranged for insertion into a connector disposed in a control module. As an example, in FIG. 2B the proximal end 248 of the lead extension 224 is inserted into a connector 250 disposed in a control module 252.

During implantation of the lead into a patient, it is sometimes desirable to test the positioning or functionality of the electrodes within the patient prior to the completion of the implantation. One way to test electrode positioning or functionality is to implant an electrode-including distal end of a lead (and, optionally, one or more lead extensions) into the patient. The proximal end of the lead (or lead extension) can then be electrically coupled to a trial stimulator that is disposed external to the patient to perform trial stimulations using the electrodes. Once it is determined that the electrodes are properly positioned and functioning within desired parameters, the trial stimulator can be removed from the proximal end of the lead (or lead extension) and replaced with a control module and the implantation can be completed.

The trial stimulations may continue for a short period (e.g., 7-10 days) where the patient is sent home with the lead, cable, and trial stimulator to assess the effectiveness of the therapy to determine if a permanent implanted system will be effective in treating the medical condition. During the trial stimulations, the lead can be electrically coupled to the trial stimulator by electrically coupling the proximal end of the lead (or lead extension) to an operating room cable ("cable") that, in turn, is electrically coupled to the trial stimulator. In some cases, when multiple leads are implanted into a patient, multiple leads (or lead extensions) may be coupled to the cable.

Figure 3:
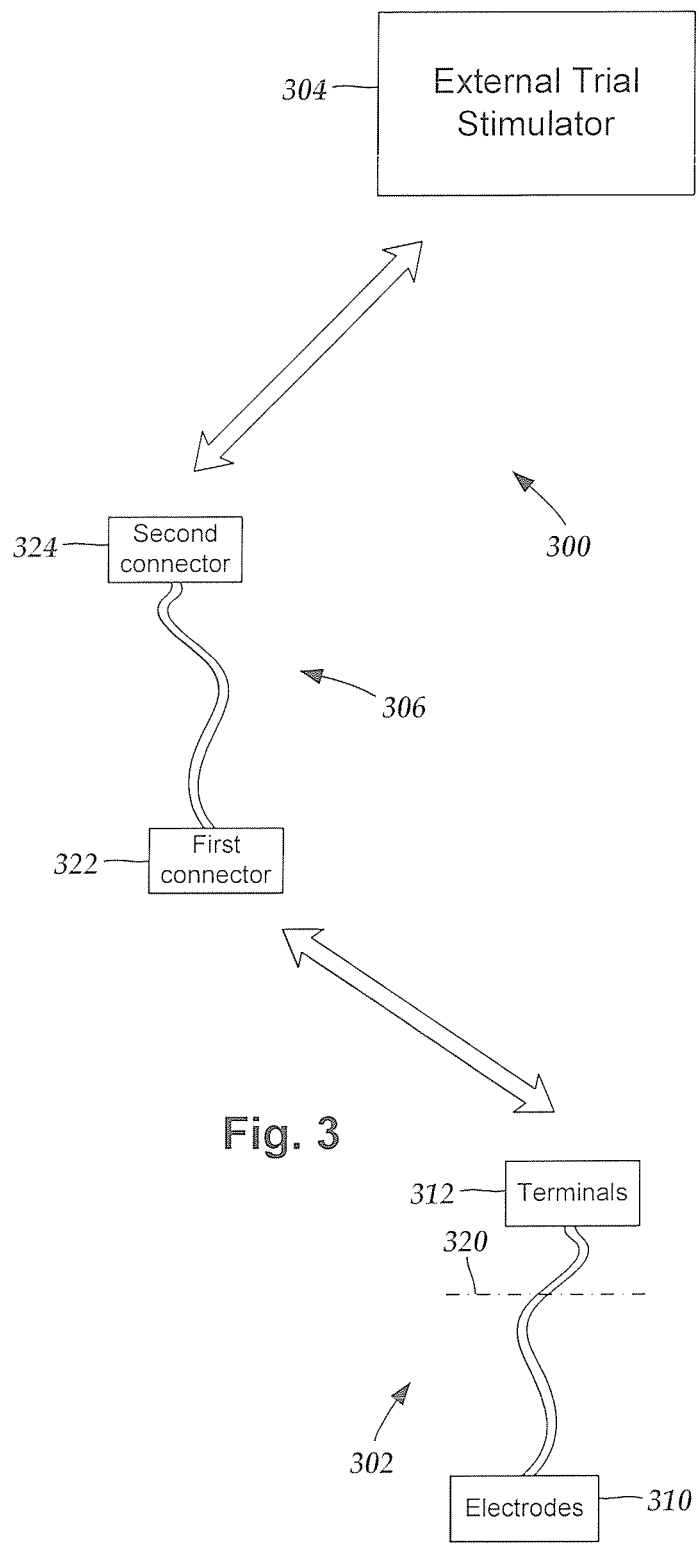
FIG. 3 is a schematic view of one embodiment of an operating room cable for electrically coupling implanted lead electrodes to a trial stimulator, according to the invention.

FIG. 3 is a schematic view of one embodiment of a trial stimulation arrangement 300 that includes a lead 302, an external trial stimulator 304, and one or more cables 306 that couple the lead 302 to the external trial stimulator 304. The lead 302 includes an array of electrodes 310 and an array of terminals 312. During operation, the electrodes 310 are disposed internal to the patient, while the terminals 312 remain external to the patient, as shown in FIG. 3 by a line 320 schematically representing patient skin. In alternate embodiments, the lead may be coupled to a lead extension, where the lead and a distal end of the lead extension are disposed in the patient while lead extension terminals remain external to the patient.

The terminals 312 are configured and arranged to couple the electrodes 310 to the external trial stimulator 304. In at least some embodiments, a lead connector 322 of the cable 306 is configured and arranged to couple to the terminals 312 of the lead 302 (or lead extension) and a trial stimulator connector 324 of the cable 306 is configured and arranged to couple to the external trial stimulator 304.

Figure 4A:
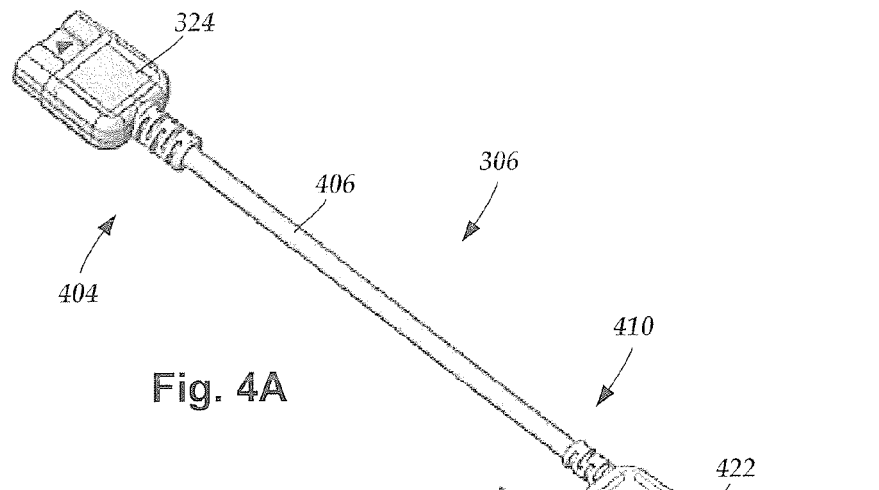
FIG. 4A is a schematic perspective view of one embodiment of the operating room cable of FIG. 3, the operating room cable having a lead connector suitable for receiving a single lead, according to the invention.
Figure 4B:
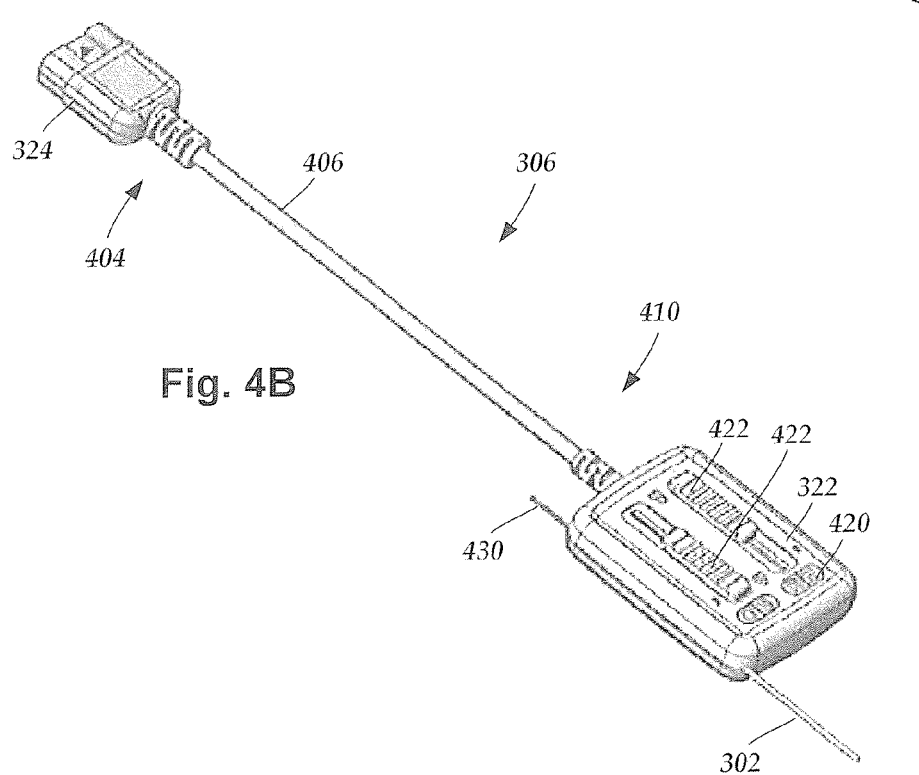
FIG. 4B is a schematic perspective view of another embodiment of the operating room cable of FIG. 3, the operating room cable having a lead connector suitable for receiving a plurality of leads, according to the invention.

FIGS. 4A and 4B illustrate two alternate embodiments of cables 306 suitable for use in a trial stimulation arrangement 300. FIG. 4A is a schematic view of one embodiment of the cable 306 suitable for receiving a single lead 302. FIG. 4B is a schematic view of an alternate embodiment of the cable 306 suitable for receiving two leads 302. The cable 306 has an elongated body 406 with the trial stimulator connector 324 disposed at a first end 404 of the body 406, and the lead connector 322 disposed at a second end 410 of the body 406. The trial stimulator connector 324 is configured and arranged to couple to the external trial stimulator (304 in FIG. 3).

The lead connector 322 includes a housing 420 configured and arranged to receive the proximal end of the lead 302 and to electrically couple terminals of the leads to connector pins electrically coupled to the trial stimulator connector 324. The lead connector 322 can be configured and arranged to receive leads with any suitable number of terminals (312 in FIG. 3) including, for example, one, two, three, four, five, six, seven, eight, nine, ten, eleven, twelve, thirteen, fourteen, fifteen, sixteen, twenty, twenty-four, twenty-eight, thirty-two, or more terminals. It will be understood that received leads may include other numbers of terminals, as well.

In some embodiments, the lead connector 322 of FIG. 4A is configured to receive a single lead 302 with eight terminals. In at least some embodiments, the lead connector 322 of FIG. 4A is configured to receive a lead with sixteen terminals. In some embodiments, the lead connector 322 of FIG. 4B is configured to receive two leads, each lead having eight terminals. In some embodiments, the lead connector 322 of FIG. 4B is configured to receive two leads, each lead having sixteen terminals. In some embodiments, the lead connector 322 of FIG. 4B is configured to receive two leads, one of the leads having eight terminals and one of the leads having sixteen terminals.

In some cases, the lead connector 322 includes a mechanical locking feature 422 configured and arranged for locking the lead 302 within the housing 420 of the lead connector 322, thereby mechanically locking the lead 302 to the cable 306. As described in more detail below, when the lead 302 is locked within the housing 420, the terminals (312 in FIG. 3) electrically couple to connector pins (506 in FIG. 5A) disposed in the housing 420. Conversely, when the lead 302 is unlocked within the housing 420, the terminals (312 in FIG. 3) are electrically uncoupled from the connector pins (506 in FIG. 5A). The locking feature 422 can be any suitable tactile feature (e.g., a slidable button, or the like). Optionally, the housing 420 and the locking feature 422 are designed such that a medical practitioner can hold the housing 420 in one hand and operate the locking feature 422 to lock or unlock the lead 302 using the same hand (e.g., using his or her thumb or one or more other fingers) without the use of a mechanical tool.

Any suitable number of locking features 422 can be used to lock the lead(s) 302 within the housing 420. In preferred embodiments, a separate locking feature 422 is associated with each different lead 302 disposed in the housing 420. For example, in FIG. 4A a single locking element 422 is shown corresponding to a single received lead 302. In FIG. 4B, although the lead connector 322 is configured to receive two leads 302, only a single lead 302 is shown disposed in the housing 420 of the lead connector 322.

Figure 5A:
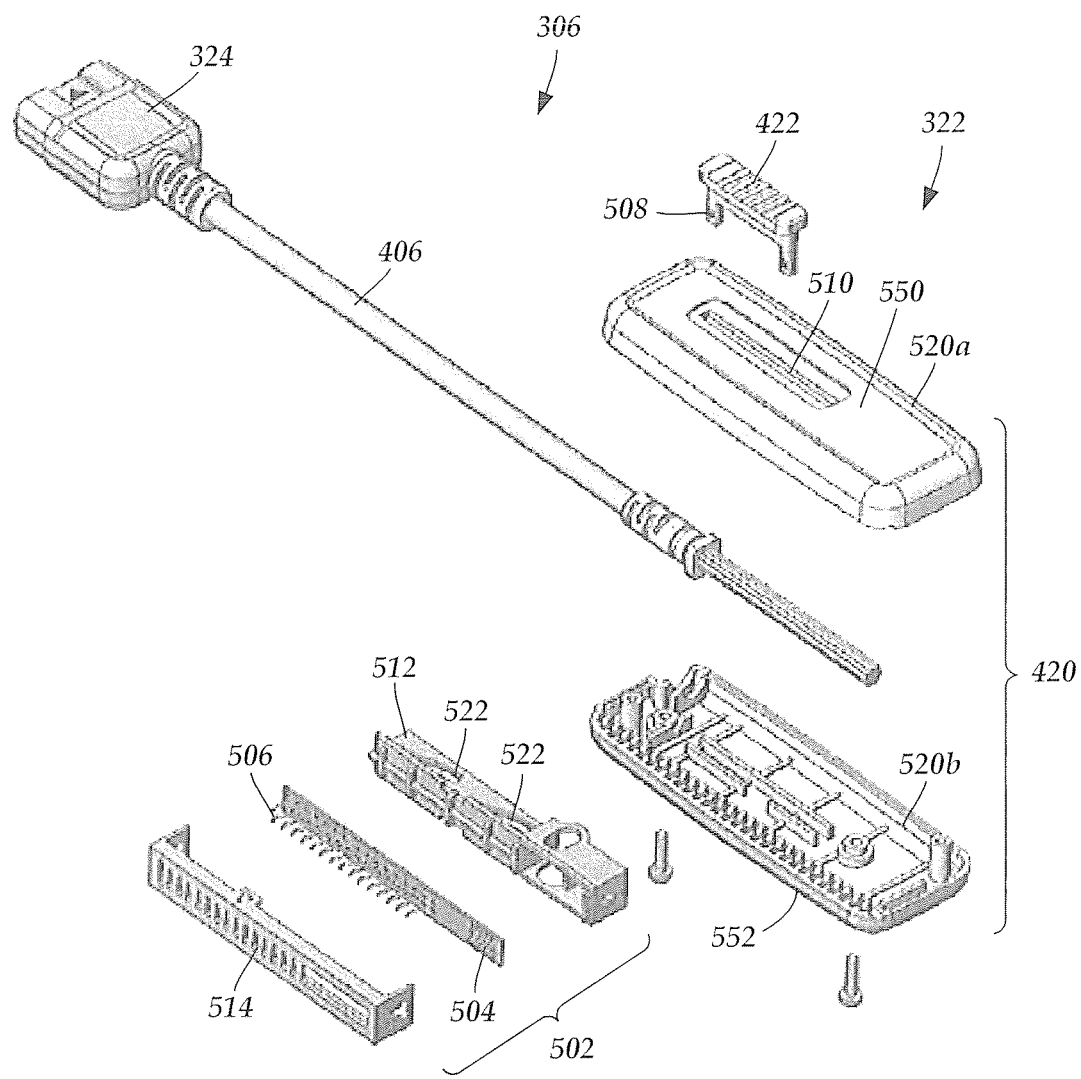
FIG. 5A is a schematic exploded, perspective view of the operating room cable of FIG. 3, the operating room cable including the lead connector of FIG. 4A, according to the invention.

FIG. 5A is a schematic exploded, perspective view of one embodiment of the lead connector 322 configured to receive a single lead 302. The lead connector 322 includes the housing 420. The housing 420 can be formed from any suitable material including, for example, plastic. In some cases, the housing 420 is formed from molded plastic. The housing 420 includes an upper casing 520a and a lower casing 520b. The upper casing 520a includes an upper major surface 550 and the lower casing 520b includes a lower major surface 552. The upper casing 520a and the lower casing 520b can be coupled together such that the upper major surface 550 and the lower major surface 552 oppose one another. The upper casing 520a and the lower casing 520b can be coupled together in any suitable manner including, for example, one or more screws, one or more snap-fit features, adhesive bonding, or the like.

A slide assembly 502, a printed circuit board 504 ("PCB"), and a plurality of connector pins 506 are each disposed within the housing 420. In at least some instances, the connector pins 506 are disposed directly on the PCB 504. The connector pins 506, in turn, are electrically coupled to conductors (not shown) that extend along a length of the body 406 and are electrically coupled to the trial stimulator connector 324.

The locking, feature 422 is disposed external to the upper casing 520a and is coupled to one or more struts 508 that pass through a locking slit 510 in the upper casing 520a. In some instances, the one or more struts 508 are coupled to the upper casing 520a. For example, in at least some embodiments the locking feature 422 is coupled to the upper casing 520a by one or more interference bumps that are molded into the sides of the one or more struts 508 and that snap-fit thru the slot 510. The one or more struts 508 couple the locking feature 422 to the slide assembly 502 such that movement of the locking feature 422 causes a corresponding movement of the slide assembly 502.

The slide assembly 502 includes a slide 512 and a slide frame 514. The slide 512 defines one or more curved slots 522 through which the one or more struts 508 extend. The PCB 504 is disposed within the slide assembly 502 such that movement of the slide assembly 502 causes a corresponding movement of the PCB 504 which, in turn, causes a corresponding lateral movement of the connector pins 506. In at least some embodiments, the PCB 504 is locked within the slide assembly 502. In at least some embodiments, the PCB 504 is bonded or snap-fit directly to the slide 512. In which case, the slide frame 514 may be omitted.

As described above, the slide 512 defines one or more curved slots 522 through which the one or more struts 508 extend. In at least some embodiments, when a user moves the locking feature 422 along the locking slit 510 in the upper casing 520a, the one or more struts 508 move along the curved slots 522. The curvature of the curved slots 522 causes lateral movement of the slide assembly 502 relative to the movement of the locking feature 522.

When the lead 302 is disposed in the lead connector 322, the lateral movement of the slide assembly 502 relative to the locking feature 422 causes the connector pins 506 to electrically couple or uncouple with the terminals 312 of the lead 302. In at least some embodiments, the movement of the locking feature 422 along the locking slit 510 is perpendicular to the movement of the connector pins 506. In at least some embodiments, the connector pins 506 move away from the locking feature 422 to electrically couple with the lead terminals (i.e., transition to a locked position), and towards the locking feature 422 to electrically uncouple from the lead terminals (i.e., transition to an unlocked position).

Figure 5B:
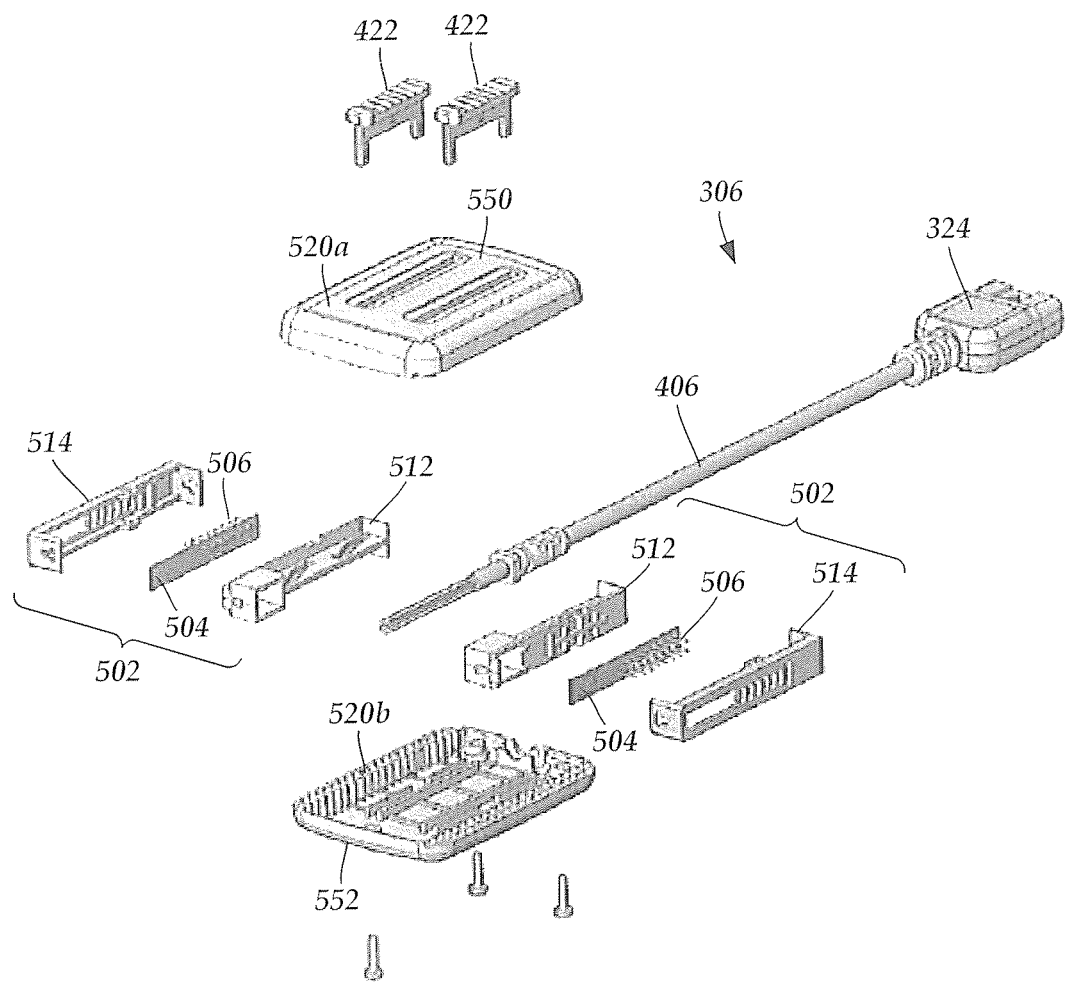
FIG. 5B is a schematic exploded, perspective view of the operating room cable of FIG. 3, the operating room cable including the lead connector of FIG. 4B, according to the invention.

FIG. 5B is a schematic exploded, perspective view of one embodiment of the lead connector 322 configured to receive a plurality of leads 302. In FIG. 5B, the lead connector 322 is configured to receive two leads 302. The components of the multi-lead-receiving lead connector 322 of FIG. 5B are similar to the components of the single-lead-receiving lead connector 322, described above with reference to FIG. 5A. The multi-lead-receiving lead connector 322 shown in FIG. 5B, however, includes a separate locking feature 422, slide assembly 502, PCB 504 and plurality of connector pins 506 for each lead 302 that the lead connector 322 is configured to receive. For example, in FIG. 5B, the lead connector 322 includes two locking features 422, two slide assemblies 502, two PCB 504, and two pluralities of connector pins 506.

Figure 6:
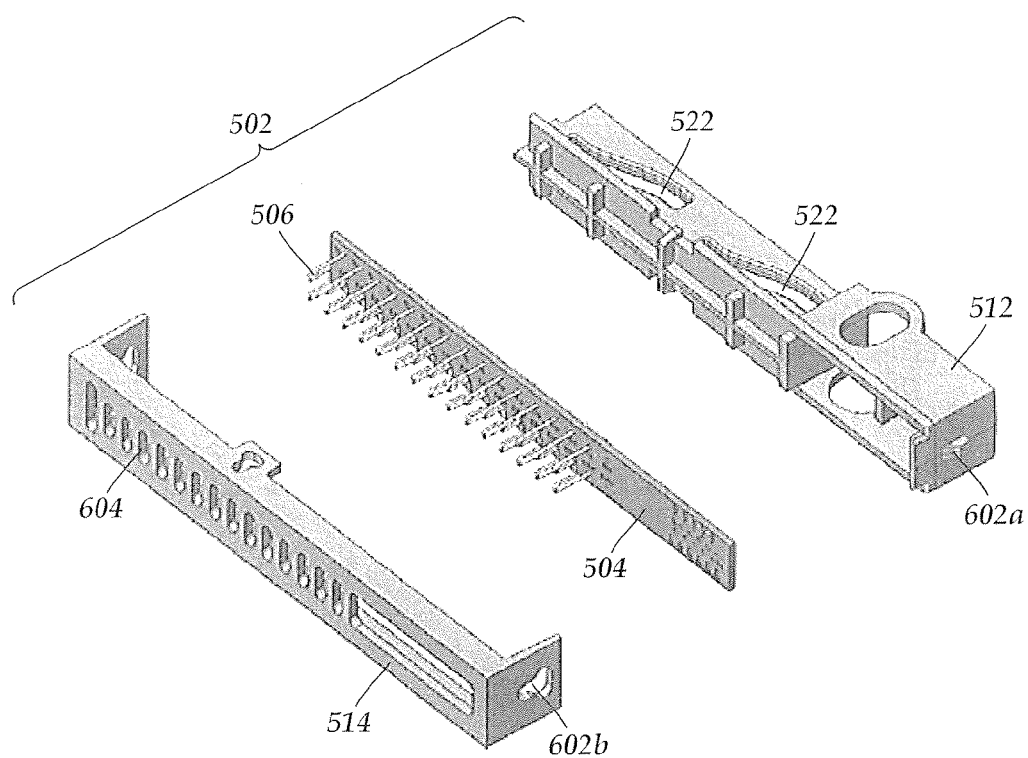
FIG. 6 is a schematic exploded, perspective view of one embodiment of a slide assembly, printed circuit board, and connector pins suitable for use with the lead connector of either FIG. 4A or FIG. 4B, according to the invention.

FIG. 6 is a schematic exploded, perspective view of the slide assembly, the PCB 504, and the connector pins 506 disposed on the PCB 504. The slide 517 and the slide frame 514 are configured and arranged to mate together and contain the PCB 504 and corresponding connector pins 506. In at least some embodiments, the slide 512 and slide frame 514 include mate-able features 602a and 602b (e.g., a slot and a corresponding tab, a protrusion and a corresponding recess, such as snap-fit features, or the like). The connector pins 506 are disposed on the PCB 504 such that the connector pins extend through connector pin apertures, such as connector pin aperture 604, defined in the slide frame 514, thereby exposing the connector pins 506 for electrically coupling to the lead 302 when the lead 302 is disposed in the lead connector 322.

In each of the embodiments of the lead connector 322 described above, with reference to FIGS. 5A-5B, the lead connectors 322 are configured to receive the lead(s) using stylets that are coupled to the leads and that engage the lead connectors from one or more sides of the lead connector (e.g., a side-loading lead connector). In the case of the embodiment of the multi-lead-receiving embodiment of the lead connector 322, the lead stylets are received on opposing sides of the lead connector 322.

It may be advantageous to design lead connectors to receive one or more leads 2) 302 via one or more stylets 430, where the stylets are received on the sides of the lead connector 322. Such a design may enable the connector to have a more narrow width than conventional lead connectors configured to receive leads (or stylets) from a top surface of the lead connector (e.g., a top-loading lead connector). Designing the lead connector to be as narrow as possible may be helpful for enabling one-handed, tool-less operation of the lead connectors by a medical practitioner during a medical procedure.

A stiffening member, such as a stylet 430, is sometimes used to adjust the positioning of a distal end of the lead 302 to a desired position within the patient. The stylet 430 is sometimes inserted into the lead 302 through a proximal end of the lead 302 such that a portion of the stylet 430 extends from the proximal end of the lead 302. The exposed portion of the stylet 430 may be used to adjust the positioning of the lead 302. It is sometimes desirable to retain the stylet 430 within the lead 302 during trial stimulation in order to facilitate further adjustment of the positioning of the lead 302 during, or subsequent to, the trial stimulation.

Stylets typically have a cap, or handle, that facilitates gripping of the stylet 430 during adjustment of the positioning of the lead 302. Conventional stylet handles have diameters that are larger than other portions of the stylet and lead and may hinder, or even prevent, a lead from coupling with a cable without first removing the stylet from the lead. As herein described, the lead connector 322 is configured and arranged to receive the lead 302 such that, when the stylet 430 is disposed in the lead 302, the stylet 430 is available for use to guide the lead 302 while the lead 302 is locked within the housing 420. In at least some embodiments, when the proximal end of the lead 302 is disposed in the housing 420, the lead 302 and the stylet 430 each extend from opposing ends of the housing 420 (see e.g., FIG. 8A).

Figure 7A:
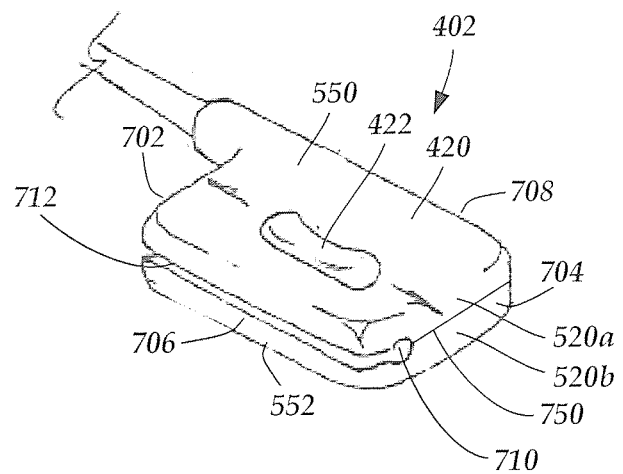
FIG. 7A is a schematic perspective view of one embodiment of the lead connector of FIG. 4A, according to the invention.

FIG. 7A is a schematic perspective view of one embodiment of the housing 420 of the lead connector 322. The housing 420 has a first end 702 and an opposing second end 704 each extending between the upper major surface 550 and the lower major surface 552. The housing 420 also has an elongated first side 706 and an opposing elongated second side 708 opposite to the first side 706. The first side 706 and opposing second side 708 each extend between the first end 702, the second end 704, the upper major surface 550, and the lower major surface 552.

The housing 420 defines a lead aperture 710 that is defined in the second end 704 of the housing 420 in proximity to the first side 706 of the housing 420. The lead aperture 710 extends from an interface 750 between the upper casing 520a and the lower casing 520b such that a portion of a circumference of the lead aperture 710 is formed by the upper casing 520a and a portion of the circumference of the lead aperture 710 is formed by the lower casing 520b.

The lead aperture 710 is continuous with an inner passage (852 in FIG. 8A) that extends along an interior of the housing 420 from the second end 704 to the first end 702. The inner passage (852 in FIG. 8A), likewise, extends along the interface 750 between the upper casing 520a and the lower casing 520b such that a portion of the walls of the inner passage is formed by the upper casing 520a and a portion of the walls of the inner passage is formed by the lower casing 520b. The lead aperture 710 and a portion of the inner passage (e.g., the portion between the second end 704 and the end stop (842 in FIG. 8A)) are configured and arranged to receive the lead 302 and, accordingly, have diameters that are no smaller than a diameter of the lead 302. In at least some embodiments, portions of the inner passage between the end stop and the first end 702 of the housing 420, have diameters that are no smaller than a diameter of the stylet 430.

A stylet slit 712 is defined in the first side 706 of the housing 420 and extends from the first end 702 to the second end 704. The stylet slit 712 extends inwardly such that the stylet slit 712 is continuous with the lead aperture 710 and the inner passage (852 in FIG. 8A). The stylet slit 712 extends along the interface 750 between the upper casing 520a and the lower casing 520b such that that one wall of the stylet slit 712 is formed by the upper casing 520a and an opposing wall of the stylet slit 712 is formed by the lower casing 520b. The stylet slit 712 is configured and arranged to enable a portion of the stylet 430 to extend through the stylet slit 712 without the lead 302 being able to extend therethrough. In at least some embodiments, the stylet slit 712 has a width that is smaller than a diameter of the lead 302 and no smaller than a diameter of the stylet 430.

It will be understood that, in other embodiments of the first connector 322, the housing 420 is configured to receive a second lead 302. In which case, the first connector 322 defines a second lead aperture, inner passage, and stylet slit in the opposing second side 708 of the first connector 322 (see e.g., FIG. 5B).

Figure 7B:
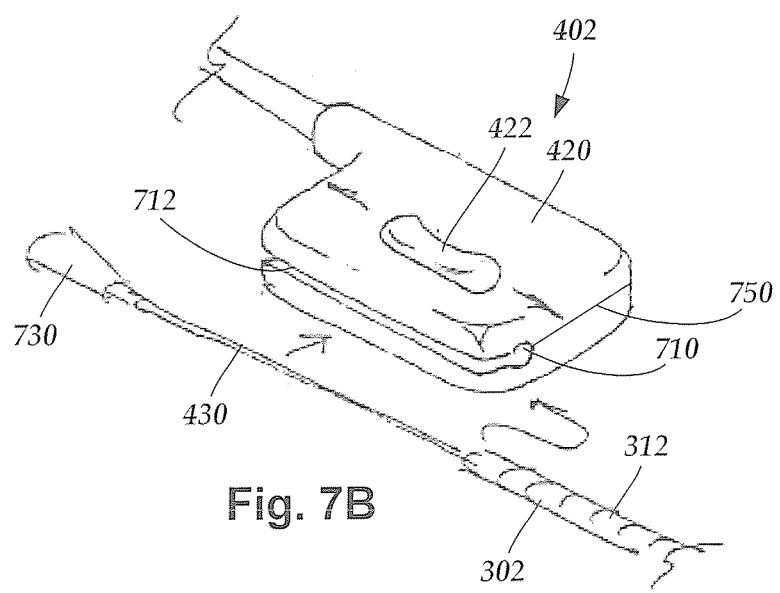
FIG. 7B is a schematic perspective view of one embodiment of a stylet extending from a portion of the lead of FIG. 3, the lead and stylet configured for insertion into the lead connector of FIG. 4A, according to the invention.

FIG. 7B is a schematic perspective view of one embodiment of the lead connector 322, a portion of the lead 302, and a portion of the stylet 430 extending from the lead 302. The stylet 430 includes a handle 730 disposed at an end of the stylet 430 extending from the lead 302. The lead aperture 710 is configured and arranged to receive the lead 302, while the stylet slit 712 is configured and arranged to receive the stylet 430. In at least some embodiments, when the lead 302 is disposed in the lead connector 322, the handle 730 of the stylet 430 extends from the first end 702, while the lead 302 extends from the second end 704. In some cases, the stylet 430 may be partially withdrawn proximally from the lead 302 prior to insertion of the lead 302 and stylet 430 into the housing 420 with the handle 730 still attached to the stylet 430.

In the case of molded plastic lead connectors, another potential advantage of loading leads from the side, as opposed to loading leads from the top of the lead connector, is that side-loading lead connectors may enable a simpler, and more robust, injection mold design than conventional top-loading lead connectors. For example, top-loading lead connectors may form one or more inner passages (e.g., lead ports) using elongated core pins. These elongated core pins are fragile and may break during the molding process. In contrast, when one or more lead apertures 710, stylet slits 712, and inner passages (852 in FIG. 8A) are each formed from portions of upper and lower casings, core pins may not be needed during the molding process.

Figure 8A:
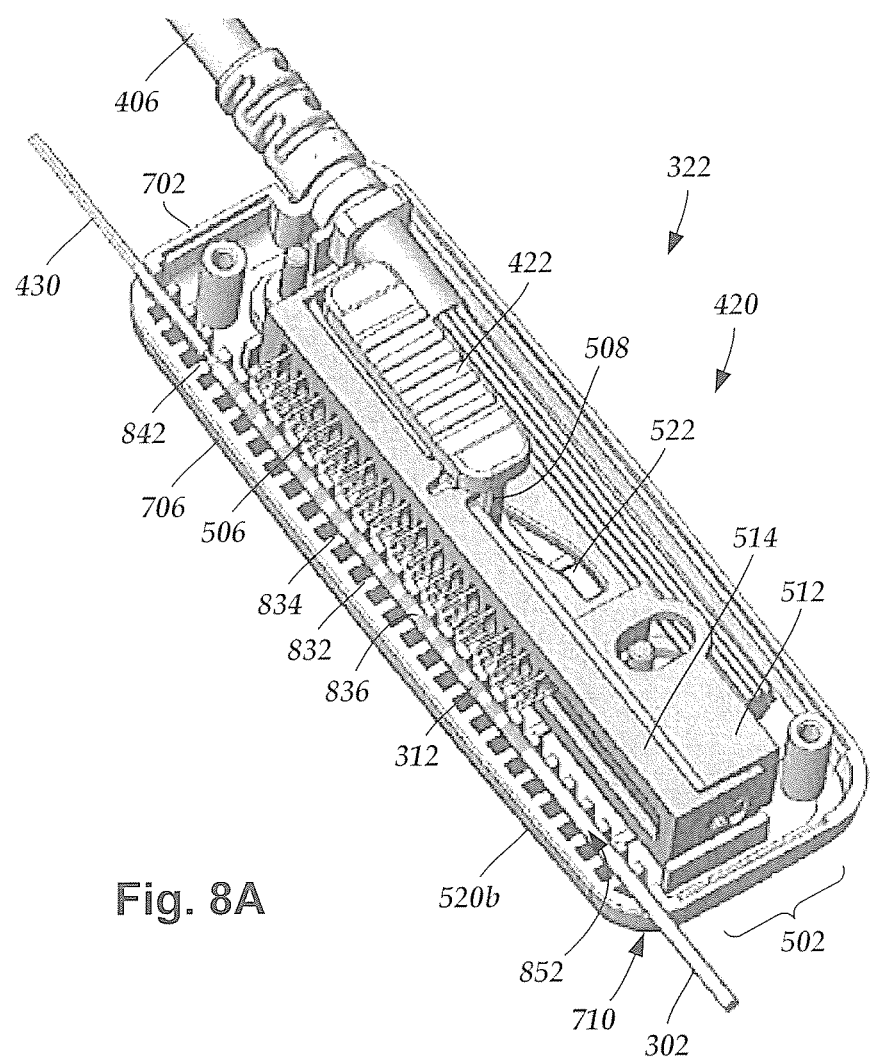
FIG. 8A is a schematic perspective view of one embodiment of the lead connector of FIG. 4A with a removed upper casing, the lead connector receiving a portion of the lead of FIG. 3 such that terminals of the lead are electrically disconnected from connector pins of the lead connector, according to the invention.
Figure 8B:
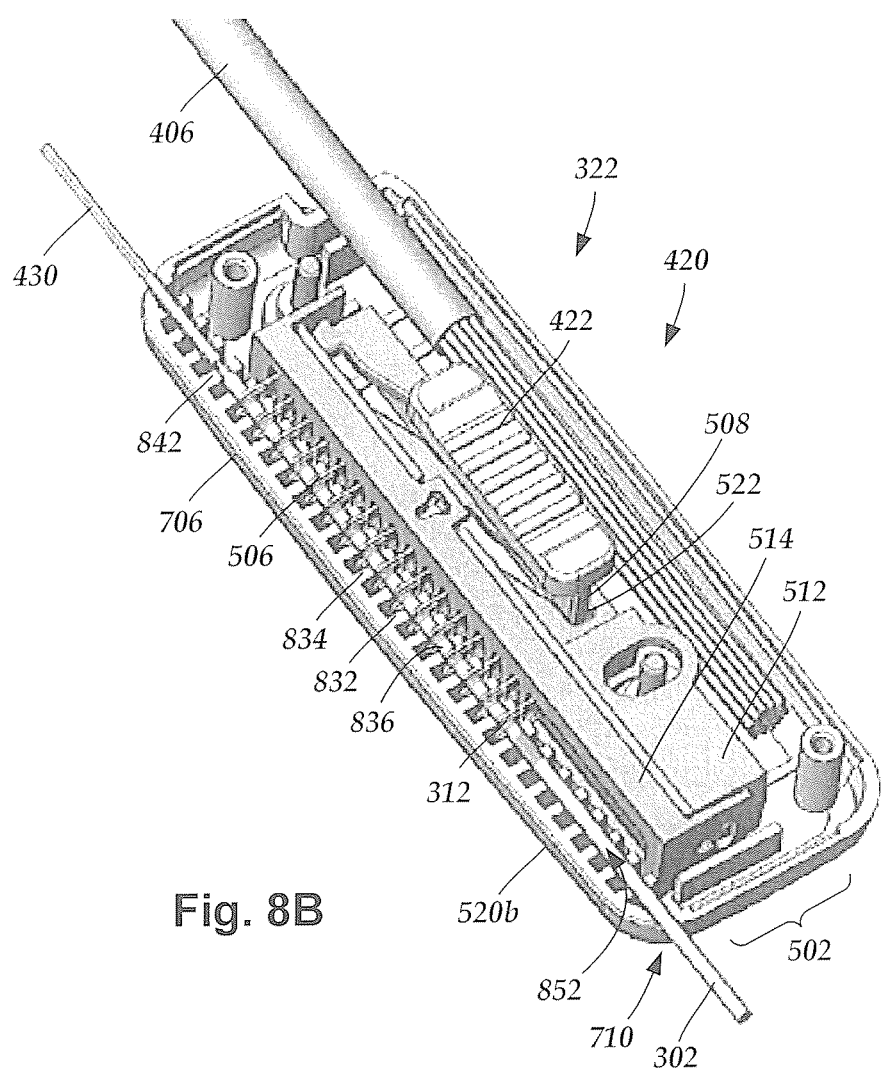
FIG. 8B is a schematic perspective view of one embodiment of the housing of FIG. 4A with a removed upper casing, the lead connector receiving a portion of the lead of FIG. 3 such that terminals of the lead are electrically connected to connector pins of the lead connector, according to the invention.
Figure 9A:
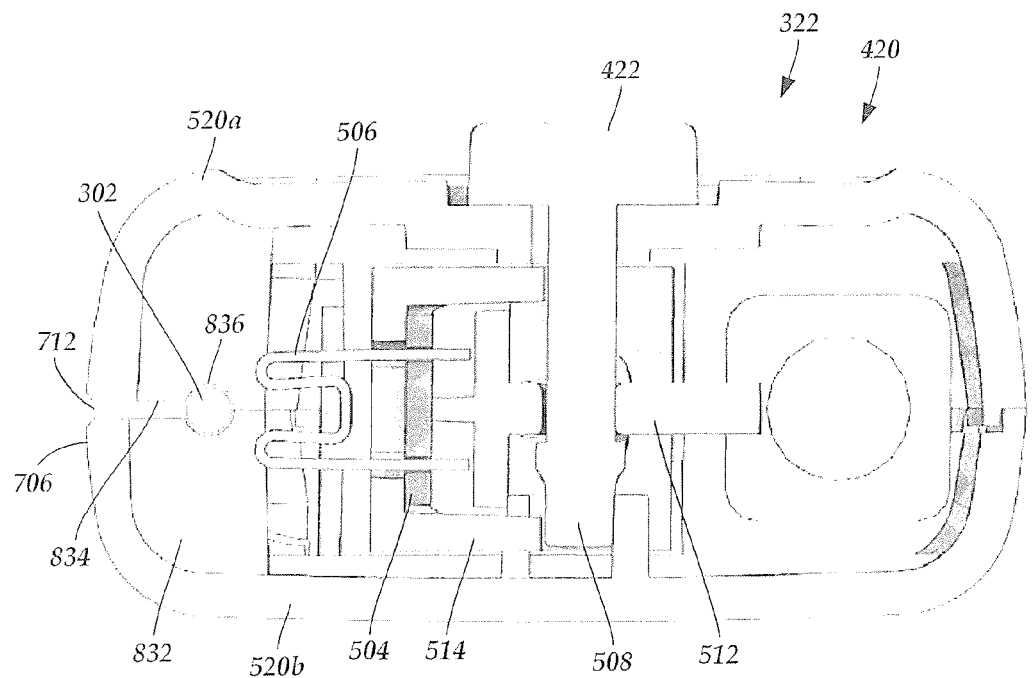
FIG. 9A is a schematic cross-sectional view of one embodiment of the lead connector of FIG. 4A receiving the lead of FIG. 3 such that terminals of the lead are electrically disconnected from connector pins of the lead connector, according to the invention.
Figure 9B:
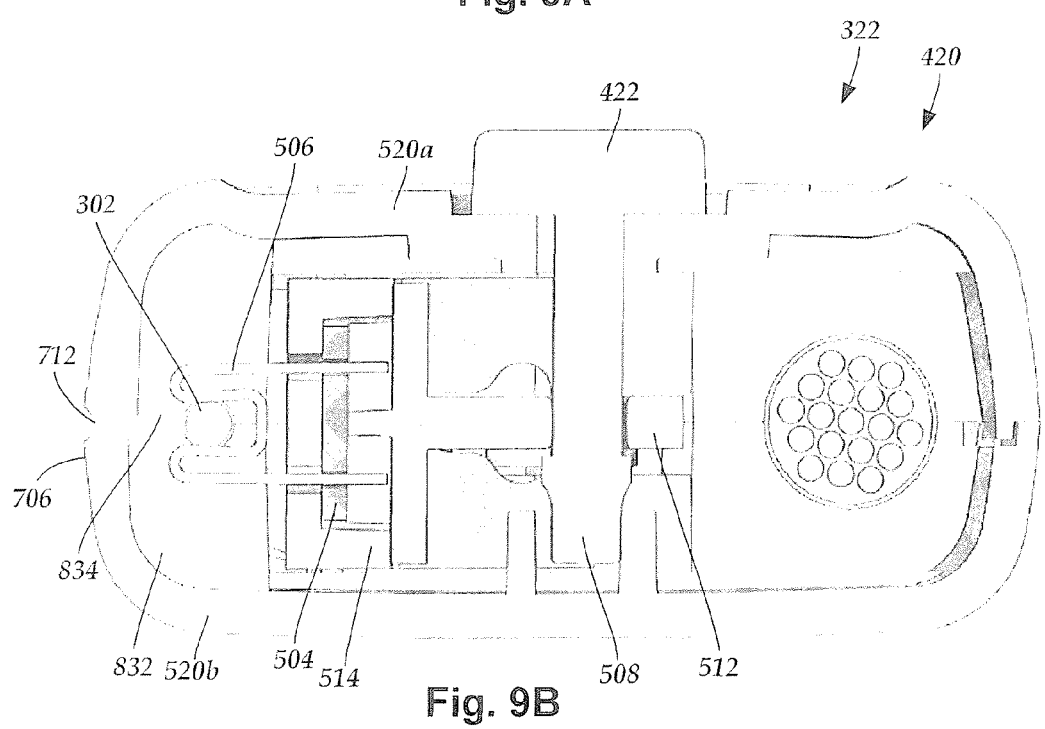
FIG. 9B is a schematic cross-sectional view of one embodiment of the lead connector of FIG. 4A receiving the lead of FIG. 3 such that terminals of the lead are electrically connected from connector pins of the lead connector, according to the invention.

FIG. 8A and FIG. 8B are schematic perspective views of one embodiment of the lead 302 and the stylet 430 disposed in the lead connector 322. FIG. 9A and FIG. 9B are schematic cross-sectional views of one embodiment of the lead 302 and the stylet 430 disposed in the lead connector 322. In FIG. 8A and FIG. 8B, the upper casing 520a of the housing 420 has been removed, for clarity of illustration.

The upper casing 520a and the lower casing 520b each include a plurality of corresponding upper and lower ribs, such as lower rib 832, which each include a flat portion 834 and a concave portion 836. Collectively, the flat portions 834 of corresponding ribs 836 of the upper casing 520a and the lower casing 520b form upper and lower edges of the stylet slit 712 and the upper and lower concave portions 836 define upper and lower guides of an inner passage 852. Thus, the ribs 832 of the upper casing 520a and the ribs 832 of the lower casing 520b each define one edge of the stylet slit 712 and a longitudinal half of the inner passage 852. In at least some embodiments, the ribs 832 function as guide channels for the connector pins 506 so that the connector pins 506 do not bend or misalign with the terminals 312 of the lead 302 when the lead 302 is inserted into the lead connector 322. In at least some embodiments, at least some of the connector pins 506 remain in engagement between two adjacent ribs 832 regardless of whether the lead connector 322 is opened or closed.

An end stop 842 is disposed in the inner passage 852. The end stop 842 controls how far along the inner passage 852 the load 302 can extend when the lead 302 is inserted into the lead aperture 710. Thus, in at least some embodiments the end stop 842 facilitates alignment of the terminals 312 with the connector pins 604 by regulating the positioning of the terminals 312 when the lead 302 is fully inserted into the lead aperture 710.

The end stop 842 can be implemented in any suitable manner. In at least some embodiments, the end stop 842 is similar in shape to a rib 832, but with one or more upper and lower concave portions (1046 in FIG. 10) that have smaller radii than the concave portions 836 of the ribs 832, thereby forming a smaller diameter when the upper and lower casings 520a,b are coupled together. For example, the end stop 842 may have a concave portion 636 of the upper casing 520a, lower casing 520b, or both that is large enough to enable the stylet 430 to extend therethrough, but small enough to prevent the lead 302 from extending therethrough.

In FIGS. 8A-9B, the terminals 312 of the lead 302 are shown disposed in the inner passage 852 such that the lead 302 rests on the ribs 832. In FIG. 8A and FIG. 9A, the locking feature 422 is disposed in a first position, where the terminals 312 of the lead 302 are electrically disconnected from the connector pins 506. In FIG. 8B and FIG. 9B, the locking feature 422 is disposed in a second position, where the slide assembly 502 has been shifted towards the first side 706, thereby electrically connecting the connector pins 506 to the terminals 312 of the lead 302.

Figure 10:
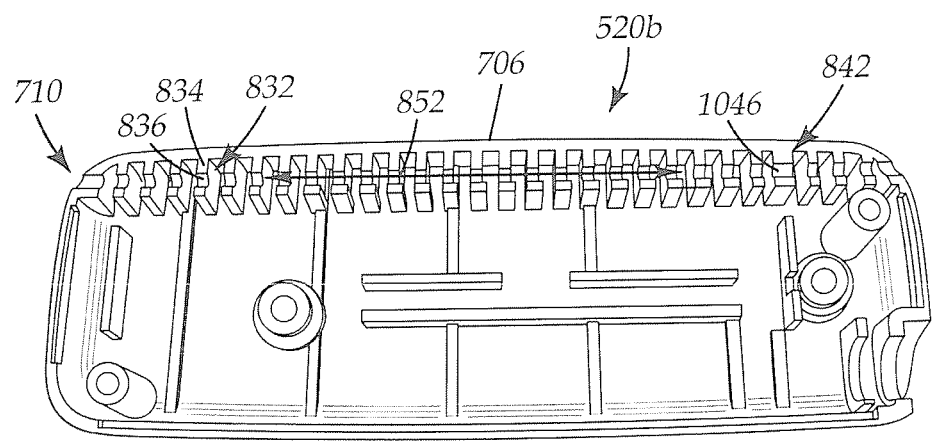
FIG. 10 is a schematic top view of one embodiment of a lower casing of the lead connector of FIG. 4A, the lower casing including a lower portion of an end stop and plurality of ribs forming a longitudinal lower half of an inner passage for insertion of the lead of FIG. 3, according to the invention.

FIG. 10 is a schematic top view of the lower casing 520b of the lead connector 402. In FIG. 10, a two-headed arrow illustrates the directionality of the inner passage 852. The flat portions 834 of the lower ribs 832 form the edges of the stylet slit (712 in FIG. 7A). The flat portions 834 extend from the first side 706 of the lower casing 520b to the concave portion 836 of the lower ribs 832. The concave portion 836 forms a longitudinal lower half of the inner passage 852.

The lower portion of the end stop 842 shown in FIG. 10 is similar in shape to the lower ribs 832, but with a concave portion 846 that has a smaller radius than the concave portion 836 of the lower rib 832. In at least some embodiments, the concave portion 846 of the end stop 842 is large enough to enable the stylet 430 to extend therethrough, but small enough to prevent the lead 302 from extending therethrough.

Figure 11:
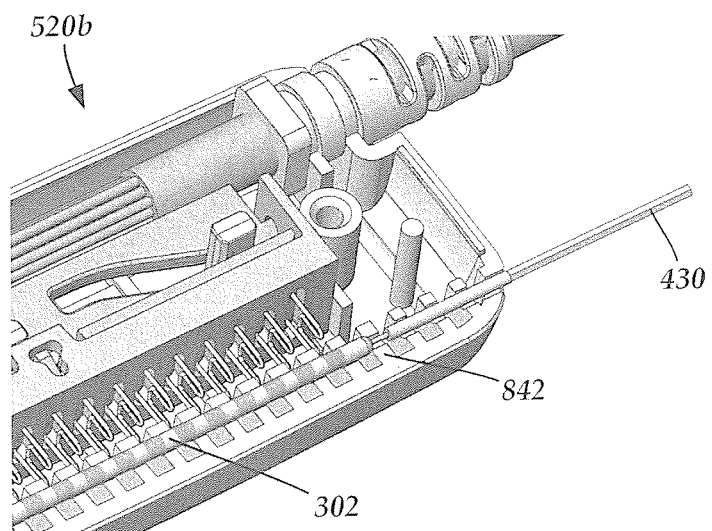
FIG. 11 is a schematic perspective view of one embodiment of a portion of the lead connector FIG. 4A with a removed upper casing, the lead connector receiving a portion of the lead of FIG. 3 such that the lead extends along a longitudinal lower half of an inner passage to a lower portion of an end stop disposed along the inner passage, according to the invention.

FIG. 11 is a schematic perspective view of a portion of another embodiment of the lead connector 402 with a removed upper casing 512a. In FIG. 11, a portion of the lead 302 is shown extending along the inner passage 852 to the end stop 842. The end stop 842 prevents the lead 302 from extending farther along the inner passage 852. The stylet 430 extends from the end of the lead 302 through the end stop 842 and to a position external to the lead connector 402.

Figure 12:
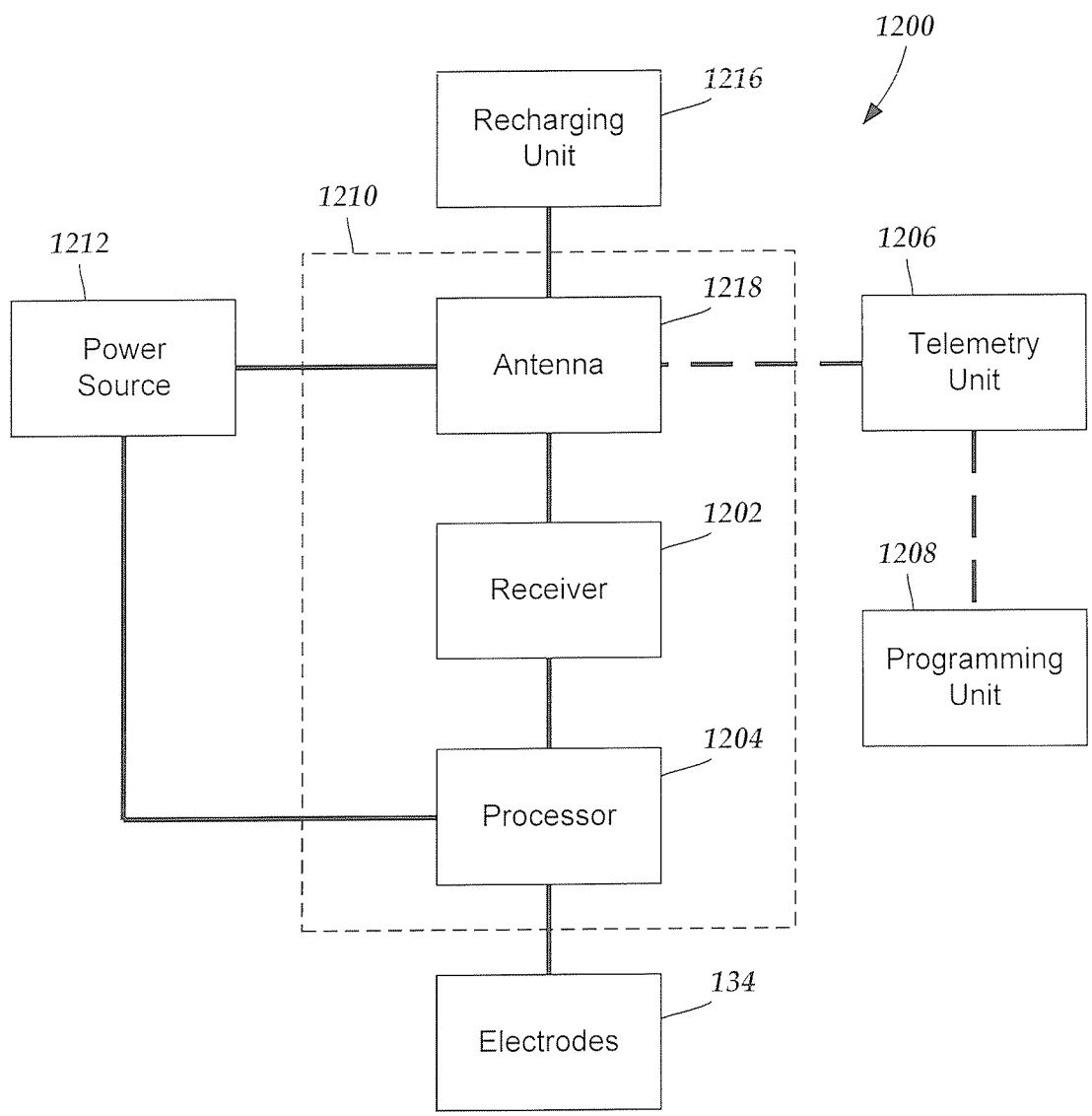
FIG. 12 is a schematic overview of one embodiment of components of a stimulation system, including an electronic subassembly disposed within a control module, according to the invention.

FIG. 12 is a schematic overview of one embodiment of components of an electrical stimulation system 1200 including an electronic subassembly 1210 disposed within a control module. It will be understood that the electrical stimulation system can include more, fewer, or different components and can have a variety of different configurations including those configurations disclosed in the stimulator references cited herein.

Some of the components (for example, power source 1212, antenna 1218, receiver 1202, and processor 1204) of the electrical stimulation system can be positioned on one or more circuit boards or similar carriers within a sealed housing of an implantable pulse generator, if desired. Any power source 1212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1218 or a secondary antenna. The external power source can be in a device that is mounted on the skin of the user or in a unit that is provided near the user on a permanent or periodic basis.

If the power source 1212 is a rechargeable battery, the battery may be recharged using the optional antenna 1218, if desired. Power can be provided to the battery fore recharging by inductively coupling the battery through the antenna to a recharging unit 1216 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1204 is generally included to control the timing and electrical characteristics of the electrical stimulation system. For example, the processor 1204 can, if desired, control one or more of the timing, frequency, strength, duration, and waveform of the pulses. In addition, the processor 1204 can select which electrodes can be used to provide stimulation, if desired. In some embodiments, the processor 1204 may select which electrode(s) are cathodes and which electrode(s) are anodes. In some embodiments, the processor 1204 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1208 that, for example, allows modification of pulse characteristics. In the illustrated embodiment, the processor 1204 is coupled to a receiver 1202 which, in turn, is coupled to the optional antenna 1218. This allows the processor 1204 to receive instructions from an external source to, for example, direct the pulse characteristics and the selection of electrodes, if desired.

In one embodiment, the antenna 1218 is capable of receiving signals (e.g., RF signals) from an external telemetry unit 1206 which is programmed by a programming unit 1208. The programming unit 1208 can be external to, or part of, the telemetry unit 1206. The telemetry unit 1206 can be a device that is worn on the skin of the user or can be carried by the user and can have a form similar to a pager, cellular phone, or remote control, if desired. As another alternative, the telemetry unit 1206 may not be worn or carried by the user but may only be available at a home station or at a clinician's office. The programming unit 1208 can be any unit that can provide information to the telemetry unit 1206 for transmission to the electrical stimulation system 1200. The programming unit 1208 can be part of the telemetry unit 1206 or can provide signals or information to the telemetry unit 1206 via a wireless or wired connection. One example of a suitable programming unit is a computer operated by the user or clinician to send signals to the telemetry unit 1206.

The signals sent to the processor 1204 via the antenna 1218 and receiver 1202 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1200 to cease operation, to start operation, to start charging the battery, or to stop charging the battery. In other embodiments, the stimulation system does not include an antenna 1218 or receiver 1202 and the processor 1204 operates as programmed.

Optionally, the electrical stimulation system 1200 may include a transmitter (not shown) coupled to the processor 1204 and the antenna 1218 for transmitting signals back to the telemetry unit 1206 or another unit capable of receiving the signals. For example, the electrical stimulation system 1200 may transmit signals indicating whether the electrical stimulation system 1200 is Operating properly or not or indicating when the battery needs to be charged or the level of charge remaining in the battery. The processor 1204 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An operating room cable for electrically coupling at least one electrical stimulation lead to an external trial stimulator, the operating room cable comprising:
   an elongated body having a first end; and
   a lead connector disposed at the first end of the body and configured and arranged to mechanically receive a proximal end of at least one electrical stimulation lead, the lead connector comprising
      a housing defining an interior and comprising a first end, a second end opposing the first end, and an elongated first side extending between the first end and the second end, a first lead aperture defined in the first end of the housing, a first inner passage extending along the interior of the housing from the first lead aperture to the second end of the housing, and a first stylet slit defined along the first side of the housing and extending from the first end of the housing to the opposing second end of the housing, wherein the first stylet slit is continuous with the first lead aperture and the first inner passage.

2. The operating room cable of claim 1, wherein the housing further defines an elongated second side extending between the first end and the second end and opposite the first side, the housing further comprising a second lead aperture defined in the first end of the housing and spaced apart from the first lead aperture, a second inner passage extending along the interior of the housing from the second lead aperture to the second end of the housing, and a second stylet slit defined along the second side of the housing and extending from the first end of the housing to the opposing second end of the housing, wherein the second stylet slit is continuous with the second lead aperture and the second inner passage.

3. The operating room cable of claim 1, wherein the housing further comprises an upper casing and a lower casing coupled to the upper casing, wherein the first stylet slit is disposed between the upper casing and the lower casing.

4. The operating room cable of claim 1 wherein the housing further comprises a plurality of upper ribs extending along the first inner passage.

5. The operating room cable of claim 4, wherein the housing further comprises a plurality of lower ribs extending the first inner passage opposite the plurality of upper ribs.

6. The operating room cable of claim 1, further comprising a first locking feature disposed on the housing and configured and arranged to move between an unlock position and a lock position, wherein in the unlock position an electrical stimulation lead received in the first lead aperture can be removed from the lead connector and in the lock position an electrical stimulation lead received in the first lead aperture is locked in the lead connector.

7. The operating room cable of claim 6, wherein the first locking feature is configured and arranged, when moved to the lock position, to actuate an electrical connection between the lead connector and an electrical stimulation lead when the lead is received by the first lead aperture.

8. The operating room cable of claim 6, further comprising at least one strut coupled to the first locking feature and extending into the interior of the housing.

9. The operating room cable of claim 8, further comprising a first slide assembly disposed in the housing, the first slide assembly defining at least one curved track that receives the at least one strut.

10. The operating room cable of claim 8, further comprising a plurality of first connector pins coupled to the first locking feature.

11. The operating room cable of claim 10, wherein the first locking feature and the at least one strut are configured and arranged such that when the first locking feature is moved from the unlock position to the lock position, the at least one strut moves with the first locking feature, the movement of the at least one strut causing a corresponding movement of the plurality of first connector pins towards the first inner passage.

12. The operating room cable of claim 10, wherein the first locking feature and the at least one strut are configured and arranged such that when the first locking feature is moved from the lock position to the unlock position, the at least one strut moves with the first locking feature, the movement of the at least one strut causing a corresponding movement of the plurality of first connector pins away from the first inner passage.

13. The operating room cable of claim 11, wherein the first locking feature and the at least one strut are configured and arranged such that when the first locking feature is moved from the unlock position to the lock position, the at least one strut moves with the first locking feature, the movement of the at least one strut causing a corresponding movement of the plurality of first connector pins in a direction that is perpendicular to the movement of the first locking feature.

14. The operating room cable of claim 1, wherein the housing further comprises an end stop disposed along the first inner passage, the end stop configured and arranged to prevent a proximal end of an electrical stimulation lead inserted into the first lead aperture from extending beyond the end stop while enabling a stylet extending from the proximal end of the electrical stimulation lead to extend beyond the end stop.

15. A trial stimulation arrangement for an electrical stimulation system, the trial stimulation arrangement comprising:
the operating room cable of claim 1;
a trial stimulator configured and arranged to generate electrical stimulation signals, the trial stimulator disposed external to a patient and coupleable to the operating room cable; and
an electrical stimulation lead having a distal end, a proximal end, a longitudinal length, and a diameter, the electrical stimulation lead comprising
a plurality of electrodes disposed along the distal end of the electrical stimulation lead.
a plurality of terminals disposed alone the proximal end of the electrical stimulation lead, and
a plurality of conductors coupling the electrodes to the terminals.

16. The trial stimulation arrangement of claim 15, further comprising a stylet having a proximal end, a distal end, and a diameter, the distal end of the stylet insertable into the proximal end of the electrical stimulation lead such that the proximal end of the stylet extends from proximal end of the electrical stimulation lead.

17. The trial stimulation arrangement of claim 16, wherein the stylet comprises a handle disposed at the proximal end of the stylet, the handle having a diameter that is larger than the diameter of the stylet.

18. The trial stimulation arrangement of claim 17, wherein the first stylet slit of the lead connector has a width that is less than a diameter of the electrical stimulation lead and not less than the diameter of the stylet.

19. A method for performing a trial stimulation on a patient, the method comprising:
providing the operating room cable of claim 1;
partially retracting a proximal end of a stylet from a proximal end of an electrical stimulation lead;
inserting an exposed portion of the partially retracted stylet into the first stylet slit of the operating room cable such that the proximal end of the electrical stimulation lead is disposed in proximity to the first end of the lead connector and a portion of the stylet extends from the second end of the lead connector;
inserting the proximal end of the electrical stimulation lead into the first lead aperture of the lead connector; and moving a first locking feature of the operating room cable to lock a plurality of pin connectors of the lead connector to terminals disposed along the inserted portion of the electrical stimulation lead.

20. The method of claim 19, further comprising electrically coupling the operating room cable to a trial stimulator.

\* \* \* \* \*